(12) United States Patent
Heller et al.

(10) Patent No.: US 8,007,622 B2
(45) Date of Patent: Aug. 30, 2011

(54) METHOD OF ASSEMBLING PERSONAL CARE ABSORBENT ARTICLE

(75) Inventors: Harold Norbert Heller, Menasha, WI (US); Donald Joseph Sanders, Larsen, WI (US); Paul Theodore Van Gompel, Hortonville, WI (US); Lori Sue Schutkoske, Butte des Morts, WI (US); Cindy Lou Price, Appleton, WI (US); Suzanne Marie Schmoker, Oshkosh, WI (US); Sarah Jane Marie Freiburger, Hortonville, WI (US); Mary Anne Bruemmer-Prestley, Appleton, WI (US); Paul William Christoffel, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 247 days.

(21) Appl. No.: 12/201,316

(22) Filed: Aug. 29, 2008

(65) Prior Publication Data
US 2009/0008030 A1    Jan. 8, 2009

Related U.S. Application Data

(60) Continuation of application No. 11/342,139, filed on Jan. 27, 2006, now Pat. No. 7,431,791, which is a division of application No. 09/834,875, filed on Apr. 13, 2001, now abandoned.

(51) Int. Cl.
*B29C 65/00* (2006.01)
*B32B 37/00* (2006.01)
*B32B 38/04* (2006.01)

(52) U.S. Cl. ......... 156/253; 156/256; 156/270; 156/302

(58) Field of Classification Search .............. 156/252, 156/253, 256, 265, 270, 302, 301
See application file for complete search history.

(56) References Cited

U.S. PATENT DOCUMENTS 5,484,505 A    1/1996  Isakson et al.
(Continued)

FOREIGN PATENT DOCUMENTS

CA    2096672    11/1997
(Continued)

OTHER PUBLICATIONS

Taiwanese Patent Abstract 382258 (date not indicated); equivalent to EP 0893115.
(Continued)

*Primary Examiner* — Philip C Tucker
*Assistant Examiner* — Sing P Chan
(74) *Attorney, Agent, or Firm* — Dority & Manning, P.A.

(57) ABSTRACT

Apparatus and methods for manufacturing personal care absorbent articles. Such personal care absorbent article includes a fastening area in the front portion for receiving fastener material thereon. First and second fault lines are formed on opposing sides of the fastening area leaving uncut web portions at the fault lines during selected manufacturing operations, thus to support machine direction stresses on the front portion web, and subsequently trimming away such uncut web portions of the fault lines. Fastener material is applied over the first and second fault lines, thus bridging the fault lines. The fastener material is releasably secured to the fastening area, non-releasably secured to the front portion outwardly of the respective fault lines, and unsecured to the front portion between the fastening area and the fault lines thus to support a re-fastening feature of such personal care absorbent articles.

12 Claims, 5 Drawing Sheets

U.S. PATENT DOCUMENTS

| | | | |
|---|---|---|---|
| 5,484,645 | A | 1/1996 | Lickfield et al. |
| 5,527,304 | A | 6/1996 | Buell et al. |
| 5,540,796 | A | 7/1996 | Fries |
| 5,578,152 | A | 11/1996 | Goulait et al. |
| 5,702,551 | A | 12/1997 | Huber et al. |
| 5,705,013 | A | 1/1998 | Nease et al. |
| 5,827,260 | A | 10/1998 | Suzuki et al. |
| 5,858,292 | A | 1/1999 | Dragoo et al. |
| 5,858,515 | A | 1/1999 | Stokes et al. |
| 5,916,203 | A | 6/1999 | Brandon et al. |
| 6,022,432 | A | 2/2000 | Elsberg et al. |
| 6,036,805 | A | 3/2000 | McNichols et al. |
| 6,046,810 | A | 4/2000 | Sanders |
| 6,113,717 | A | 9/2000 | Vogt et al. |
| 6,124,001 | A | 9/2000 | Sugita et al. |
| 6,375,646 | B1 | 4/2002 | Widlund et al. |
| 6,454,888 | B1 | 9/2002 | Murie et al. |
| 6,524,293 | B1 | 2/2003 | Elsberg et al. |
| 6,682,626 | B2 | 1/2004 | Mlinar et al. |
| 6,702,801 | B2 | 3/2004 | Gompel et al. |
| 7,431,791 | B2 * | 10/2008 | Heller et al. .................. 156/253 |
| 2002/0045879 | A1 | 4/2002 | Kamari |
| 2002/0151422 | A1 | 10/2002 | Duhm et al. |
| 2002/0157778 | A1 | 10/2002 | Sorenson et al. |
| 2002/0169432 | A1 | 11/2002 | Fell et al. |
| 2003/0004487 | A1 | 1/2003 | Gompel et al. |
| 2003/0028166 | A1 | 2/2003 | Price et al. |
| 2003/0055389 | A1 | 3/2003 | Sanders et al. |
| 2003/0088223 | A1 | 5/2003 | Vogt et al. |
| 2003/0124303 | A1 | 7/2003 | Price et al. |
| 2003/0132549 | A1 | 7/2003 | Mlinar et al. |
| 2003/0135184 | A1 | 7/2003 | Van Gompel et al. |
| 2003/0135191 | A1 | 7/2003 | Price et al. |
| 2003/0135192 | A1 | 7/2003 | Guralski et al. |

FOREIGN PATENT DOCUMENTS

| | | |
|---|---|---|
| EP | 0809992 | 12/1997 |
| EP | 0893115 | 1/1999 |
| GB | 2308290 | 6/1997 |
| JP | 2002-046491 | 2/2001 |
| WO | WO 9104724 | 4/1991 |
| WO | WO 9818421 | 5/1998 |
| WO | WO 0020208 | 4/2000 |
| WO | WO 0037009 | 6/2000 |
| WO | WO 0182852 | 11/2001 |
| WO | WO 0241816 | 5/2002 |

OTHER PUBLICATIONS

US 5,915,536, 06/1999, Alberts et al. (withdrawn)

* cited by examiner

METHOD OF ASSEMBLING PERSONAL CARE ABSORBENT ARTICLE

RELATED APPLICATIONS

The present application is a continuation of U.S. patent application Ser. No. 11/342,139 filed Jan. 27, 2006, now U.S. Pat. No. 7,431,791, which is a divisional application of U.S. patent application Ser. No. 09/834,875 filed Apr. 13, 2001, now abandoned. The present application claims priority to both of these applications, and their disclosures are incorporated by reference herein.

BACKGROUND OF THE INVENTION

This invention relates to apparatus and methods for assembly of personal care absorbent articles, as well as to such personal care absorbent articles. More specifically, this invention relates to methods of assembly and apparatus for assembling especially re-fastenable personal care absorbent articles wherein the methods of the invention attenuate certain counterproductive aspects of conventional manufacture of such personal care absorbent articles. While embodiments of the present invention are described herein in terms of personal care absorbent articles such as pull-on pants or adult incontinence briefs, the invention includes, and is equally applicable to a wide variety of articles fabricated in web formats, such products as infant diapers, training pants, and the like.

In conventional methods for fabricating disposable personal care articles, it is known to fold over a web or webs of a stream of workpieces at a first, relatively earlier stage in the manufacturing process to form a stream of individual personal care article precursors.

Yet other conventional methods reflect adjacent personal care article precursors being attached to one another along the stream of workpieces by e.g. front portion material, wherein the front portion material is cut out or apart to separate such articles at the end of the process. Associated with the second, relatively later stage of conventional manufacturing processes is the excision and removal of significant cut-out portions affiliated with e.g. front portion materials, leg cut-out regions, and/or trim between side seams of adjacent articles, from the web or webs resulting in significant material waste attributable to such inefficient conventional manufacturing processes.

A need exists for improved methods for production of personal care absorbent articles wherein the methods are effective to attenuate waste in a manufacturing process as well as to reduce cost inevitably associated with inefficiency of such manufacturing process.

Thus, it is an object of this invention to provide methods for production of personal care absorbent articles which methods maintain unsegmented streams of workpieces, without severing respective front portions and rear portions from a respective web sausage, until relatively late in the process, with respect to conventional methods, thereby enabling manufacturers of personal care articles to integrate personal care article components into the web sausage in the context of an entire stream of workpieces rather than individual workpiece precursors.

It is another object of this invention to provide methods for the production of personal care absorbent articles which methods improve control and stability of the stream of workpieces as such stream of workpieces is affected along the manufacturing line.

It is a further object to provide manufacturing processes which reduce cost to manufacturers by enabling a manufacturer to minimizing on-line material waste associated with the manufacturing process.

SUMMARY OF THE DISCLOSURE

In a first family of embodiments, the invention comprehends a method of manufacturing personal care absorbent articles in a format which includes defining a stream of workpieces connected to each other along a web sausage having an indefinite length. Each of respective such personal care articles has a front portion including a front edge, a rear portion, and a crotch portion between the front portion and the rear portion. The method comprises, for a given workpiece in the web sausage, defining the front portion, the rear portion, and the crotch portion, and defining a fastening area in the front portion for receiving fastener material thereon. The method also comprises forming first and second fault lines in the workpiece on opposing sides of the fastening area, the first and second fault lines being oriented in directions generally extending between the front portion and the rear portion when a blank of the workpiece is laid out flat. Additionally, the method comprises applying fastener material over the respective first and second fault lines. The fastener material, as applied, extends across, and thus bridges, the respective fault lines. The fastener material is releasably secured to the fastening area, is non-releasably secured to the front portion outwardly of the respective fault lines, and is unsecured to the front portion between the fastening area and the fault lines. The method also comprises separating individual such workpieces from the web sausage as such personal care articles.

In preferred embodiments, the method includes cutting leg cut-outs in the web sausage between the respective workpiece and adjacent workpieces, and correspondingly cutting into the respective fault lines in so cutting the leg cut-outs.

In preferred embodiments, each of the first and second fault lines is formed as a cut line of one or more elongate cuts and minor, if any, web connections therebetween, with uncut web portions at opposing ends of the cut line, sufficiently strong, in combination, to support integrity of the front portion across the fault lines. The cutting into the fault lines in cutting the leg cut-outs is effective to remove the uncut web portions adjacent the leg cut-outs and to thereby communicate with the cut line. The method further includes separating material along a front edge of the workpiece thereby to form the front edge of the personal care article and to separate the substantial uncut web portion at the front edge and thereby further communicate with the cut line, such that the fastener material provides primary support of the front portion across the fault lines.

In some embodiments, the method includes forming each of the first and second fault lines as a cut line of one or more elongate cuts and minor, if any, web connections therebetween, with substantial uncut web portions at opposing ends of the fault line, wherein the cutting into the fault line at the cutting of the leg cut-out comprehends removing the entirety of the uncut web portion at the respective end of the fault line.

In other embodiments, the method includes forming each of the first and second fault lines as a cut line of one or more elongate cuts and minor, if any, web connections therebetween, with relatively shorter-length perforation cuts and corresponding effective uncut web support connections between such perforation cuts at opposing ends of the one or more elongate cuts.

In preferred embodiments, the method further includes separating material along a front edge of the workpiece thereby forming the front edge of the personal care article and thus removing the effective support connections at the front edge, such that the fastener material provides primary support of the front portion across the fault lines.

In yet other embodiments, the method includes forming each of the first and second fault lines as a line of relatively uniformly formed and uniformly spaced perforations.

Some embodiments can include cutting leg cut-outs between the respective workpiece and adjacent workpieces in the web sausage, and correspondingly removing first perforated end portions of the respective fault lines in so cutting the leg cut-outs, and separating material along a front edge of the workpiece and thereby forming the front edge of the personal care article, and correspondingly, separating second perforated end portions of the respective fault lines at the front edge, such that the fastener material provides substantial support of the front portion across the fault lines in combination with support provided by web connections between respective ones of the perforations.

In still other embodiments, the method includes forming each of the first and second fault lines as a line of relatively uniform perforations with relatively short and uniform uncut web portions between the respective perforations, and relatively longer uncut web portions at opposing ends of the respective line of perforations.

Some embodiments include cutting leg cut-outs between the respective workpiece and adjacent workpieces in the web sausage, and correspondingly removing portions of the respective fault lines in so cutting the leg cut-outs, the removing of the portions of the fault lines in cutting the leg cut-outs being effective to remove uncut web portions adjacent the leg cut-outs and to communicate with the line of perforations. The method can further include separating material along a front edge of the workpiece thereby to form the front edge of the personal care article and separating the substantial uncut web portion at the front edge to thereby further communicate with the line of perforations, such that the fastener material provides substantial support of the front portion across the fault lines.

In even yet other embodiments, the method includes forming the fault lines as pressure lines which are defined by a process of crushing web material which responds to a crushing force, using a dull knife against an anvil roll, and reserving uncrushed web portions at least at opposing ends of the respective pressure lines.

In some embodiments, the method includes employing, as the fastening material, first and second fasteners extending across, and thus bridging, the respective first and second fault lines.

Some embodiments can include the first and second fasteners employing first fastening material effective to interact with second different fastening material in the fastening area.

In preferred embodiments, the method includes fabricating such personal care article using first and second front and rear portion webs, including bringing the rear portion web and the front portion web into facing relationship with each other, and forming side seams connecting the front and rear portion webs to each other, outwardly of such fault lines, thereby to form individual workpiece precursors of such personal care articles, having joined front and rear portions.

In a second family of embodiments, the invention comprehends a method of manufacturing personal care absorbent articles having leg openings on opposing sides of the crotch portion. The method comprises, for a given workpiece, forming first and second fault lines in the workpiece on opposing sides of the fastening area. The first and second fault lines generally extend from a front edge of the workpiece to the respective leg openings, and the first and second fault lines have centrally located relatively weaker portions and relatively stronger portions adjacent the leg openings and the front edge. The method also includes applying first and second fasteners over the respective first and second fault lines, releasably securing the first and second fasteners to the fastening area, and non-releasably securing the first and second fasteners to the front portion outwardly of the respective fault lines, as well as maintaining the first and second fasteners unsecured to the front portion between the fastening area and the fault lines. Additionally, the method includes cutting away the relatively stronger portions of the fault lines adjacent the leg openings and adjacent the front edge thereby to form the front edge, such that material of the front portion is precluded from independently supporting the integrity of the front portion across the fault lines. The method also includes separating individual such workpieces from the web sausage as such personal care articles.

In preferred embodiments, the method includes cutting away the relatively stronger portion adjacent the leg openings concurrently with forming at least a portion of the respective leg opening in a workpiece precursor of such personal care article.

In preferred embodiments, the method includes cutting away the relatively stronger portion adjacent the front edge concurrently with forming the front edge in a workpiece precursor of such personal care article.

In a third family of embodiments, the invention comprehends a method of manufacturing personal care absorbent articles having leg openings on opposing sides of the crotch portion and between the front portion and the rear portion. The method comprises drawing a front portion web and a rear portion web in parallel and transversely spaced juxtapositions along an operations path. The method also comprises defining fastening areas in the front portion web, and thereby defining locations in the front portion web for development of respective workpieces in combination with adjoining areas of the rear portion web. Additionally, the method comprises forming first and second fault lines in the front portion web, on opposing sides of the respective fastening areas. The first and second fault lines are oriented in directions generally extending between the front portion web and the rear portion web when the front portion web and the rear portion web are displaced from each other and arranged in a common relatively flat surface. The first and second fault lines have centrally located relatively weaker portions and relatively stronger end portions adjacent the leg openings and adjacent the front edge of the respective workpiece. Additionally, the method includes' applying fastener material over the respective first and second fault lines, the fastener material, as applied, extending across, and thus bridging, the respective fault lines, and being releasably secured to the fastening area, being non-releasably secured to the front portion web outwardly of the respective fault lines, and being unsecured to the front portion web between the fastening area and the fault lines. The method also comprises securing crotch elements to the front portion web and the rear portion web at respective workpiece locations, and thereby defining the respective workpieces and providing transverse direction linking connections between the front portion web and the rear portion web at the respective workpieces. The method further includes cutting away the relatively stronger end portions of the fault lines such that material of the front portions of the resulting personal care articles are precluded from independently supporting integrity of the front portions of the personal care articles across such fault lines. The method further comprises bringing the rear portion web and the front portion web into folded over engaging relationship with each other and forming side seams between the front portion web and the rear portion web outwardly of the fault lines on a respective workpiece, thereby to define individual personal care articles. The method also includes separating individual such personal care articles from the web sausage, thereby to form individual such personal care articles.

In some embodiments, the method further includes separating material along the front portion web thereby to form the front edges of the personal care articles and to separate the substantial uncut web portion at the front edge and to thereby further to communicate with the cut line, such that the fastener material provides primary support of the front portion across the fault lines. In such embodiments, the fault lines are formed as cut lines of one or more elongate cuts and minor, if any, web connections therebetween, with uncut web portions as the stronger end portions sufficiently strong, in combination, to support integrity of the front portion across the fault lines. The cutting into the fault lines in cutting the leg cut-outs is effective to remove the uncut web portions adjacent the leg cut-outs and to thereby communicate with the cut line.

In some embodiments, the method includes forming the fault lines as cut lines each having one or more elongate cuts and minor, if any, web connections therebetween, with uncut web portions as the relatively stronger end portions of each fault line, and wherein the cutting into the fault lines at cutting of the leg cut-outs comprehends removing the entirety of the relatively stronger uncut web end portions at the respective ends of the fault lines.

In other embodiments, the method includes forming respective such fault lines as cut lines of one or more centrally-disposed elongate cuts and minor, if any, web connections therebetween, with relatively shorter-length perforation cuts and corresponding effective uncut web support connections between such perforation cuts at the relatively stronger ends.

In yet other embodiments, the method includes forming the fault lines as lines of relatively uniform perforations with relatively short and uniform uncut web portions between the respective perforations, and relatively longer uncut web portions at opposing ends of the respective lines of perforations.

In a fourth family of embodiments, the invention comprehends a personal care absorbent article comprising a front portion including an outer front edge and opposing first and second side edges, a rear portion including an outer rear edge, and a crotch portion extending between the front portion and the rear portion. These embodiments also comprise leg openings on opposing sides of the crotch portion, wherein the leg openings can define a first inner end of the front portion and can define a second inner end of the rear portion. Additionally, these embodiments comprise a fastening area disposed on the front portion inwardly of the first and second side edges, and first and second fault lines in the front portion which preclude material of the front portion from independently supporting integrity of the front portion across such fault lines, the respective first and second fault lines being disposed between the fastening area and the respective first and second side edges. These embodiments also comprise first and second fasteners releasably secured to the fastening area, non-releasably secured to the front portion outwardly of the respective fault lines, and unsecured to the front portion between the fastening area and the fault lines.

In some embodiments, the fault lines are cut lines with no front portion material extending across the fault lines.

In other embodiments, the fault lines comprise lines of perforations with limited lengths of front portion material extending across the fault lines.

In preferred embodiments, the fasteners comprise hook-type fasteners engageable with loop material at the fastening area.

In a fifth family of embodiments, the invention comprehends a method of manufacturing personal care absorbent articles comprising forming first and second fault lines in the workpiece on opposing sides of the fastening area, wherein the first and second fault lines generally extend substantially from the front edge of the workpiece to the respective leg openings. In such embodiments, the first and second fault lines have points of web-attachment sufficient, in combination, to maintain the integrity of the workpiece as such workpiece proceeds through manufacture.

Each point of web-attachment is generally defined between adjacent cuts and/or perforations on a respective fault line.

Figure 1A:
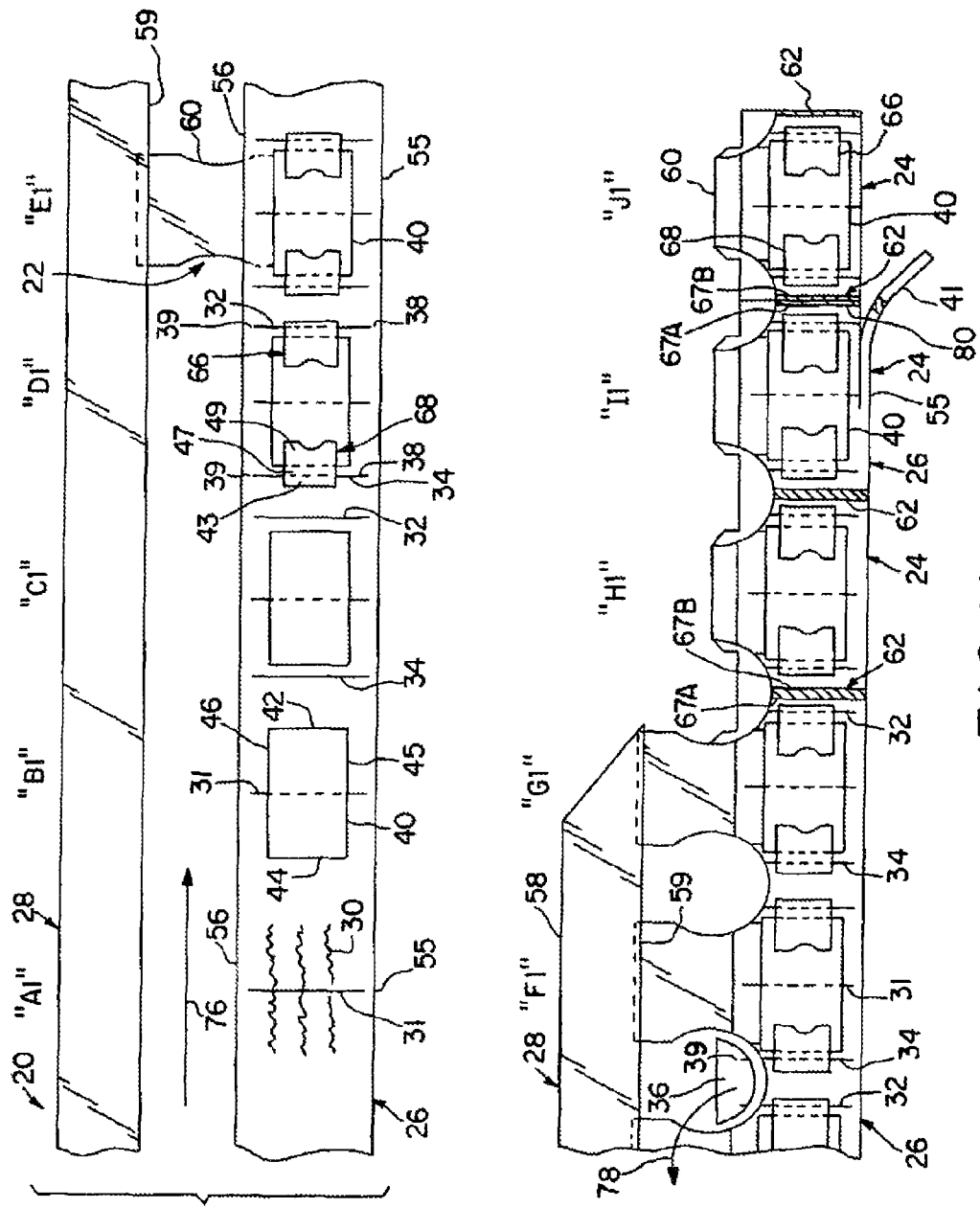
FIG. 1A shows a representative top view of a stream of workpieces indicative of some methods of the invention.

The invention is not limited in its application to the details of the construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components.

DETAILED DESCRIPTION OF THE ILLUSTRATED EMBODIMENTS

Referring to FIG. 1A, the invention comprehends apparatus and methods for assembling personal care absorbent articles. Respective segments of the exemplary illustrated manufacturing process of the invention are indicated by letters "AI-JI".

At the segment of the method illustrated at "AI", a stream of workpieces 20 travels along a manufacturing path in the machine direction indicated by directional arrow 76. In the embodiment illustrated in FIG. 1A, stream of workpieces 20 is defined in the combination of front portion web 26 and rear portion web 28, as well as any other personal care article components employed or affixed, both directly and indirectly, to such webs. At segment "AI" of the process illustrated in FIG. 1A, strands of elastic 30 are disposed on and/or in front portion web 26. While FIG. 1A shows elastic strands 30 only at a central portion of the workpiece in segment "AI", it should be understood that such elastic strands are typically spaced along the full widths, and extend along the full lengths, of webs 26 and 28, and that such properties generally carry through to all of process segments "AI-JI".

While only front portion web 26 is illustrated comprising elastic 30 in FIG. 1A, preferred embodiments comprise elastic at least in and/or on portions of one or both of front portion web 26 and rear portion web 28. Other less preferable embodiments comprise no elastic in and/or on one or both front portion web 26 and rear portion web 28. Yet in other embodiments, one or both front portion web 26 and back portion web 28 comprise web materials which demonstrate resiliently stretchable properties such as stretch-bonded laminate materials and neck-bonded laminate materials, as well as other composite elastomeric materials and/or resiliently stretchable materials known to those of ordinary skill in the art.

Regardless of the elastic properties selected, manufacture of personal care absorbent articles of the invention is designed and configured such that at least portions, if present, of elastic 30 disposed on and/or in front portion web 26 are generally severed or otherwise deactivated before or during processing of stream of workpieces 20. Yet some embodiments of the invention are designed and configured such that substantially none of the elastic of one or both front portion web 26 or back portion web 28 are deactivated prior to or during the manufacturing process.

Segment "AI" of the process illustrates elastic 30 being severed along a path substantially perpendicular to machine direction 76 at deactivation line 31. Elastic strands disposed on and/or in webs 26, 28 can be deactivated by severing such elastic using e.g. a rotary die cutter, by melt-breaking such elastic using e.g. a heated or ultrasonic function roll, or by any other means known to those skilled in the art for deactivating elastics. In preferred embodiments, deactivation line 31 does not extend closer than about 0.25 inch from either outer edge 55 or inner edge 56 of front portion web 26. Such deactivation deactivates the elastic only at those portions of the respective elastic strands which are not secured to the respective e.g. web 26. Thus, upon severance, the elastic strands, to the extent stretched, and not bonded to the web; retract into a generally unstressed condition. The area over which the elastic strands so retract, suggested by the wavy lines at segment "AI", are thenceforth inactive as far as resilient stretching imparted by the elastics.

At segment "BI" of the manufacturing process, a patch of fastening material 40 comprising landing zone material overlies at least a portion of the area deactivated by the severing of elastics at deactivation line 31, to maintain the integrity of front portion web 26, which tends to be affected by tension forces acting in the machine direction. The patch of landing zone material, comprising a fastening area, can be affixed to front portion web 26 by e.g. applying a suitable adhesive to the landing zone material patch or to the front portion web and affixing the fastening area to front portion web 26 using e.g. a cut-and-place applicator.

The patch of landing zone material comprises a fastening area 40 typically encompassing substantially the entireties of the lengths and the widths of such patch of landing zone material. The patch of landing zone material typically includes a first side 42, a second side 44, a top edge 45, and a bottom edge 46. The first and second sides 42, 44 of the patch of landing zone material are defined in relationship with deactivation line 31. While patch 40 is illustrated as being a one-component, generally rectangular-shaped piece of landing zone material, the fastening area can be defined by a variety of shapes and sizes, and any desired number of separate components. Preferably, patch or patches 40 are designed and configured so as to contribute to the maintenance of the integrity and dimensional stability of front portion web 26 at a portion of deactivation line 31 as a result of the application of the respective fastening patch 40.

Fastening area 40 can be constructed from a material which preferably has e.g. loop properties or hook material properties. In the alternative, any material which can form a cooperative relationship with desired fastener materials, such as those suggested in the discussion of segment "D" of the process, to provide repeatable fastening and releasing properties while maintaining the integrity of front portion web 26, is suitable for use as, or in place of, fastening area 40.

In some embodiments, front portion web 26 comprises a material which demonstrates landing zone properties capable of forming engagement relationships with respective fastener materials defined in step "D" of the process. In such embodiments, step "BI" of the manufacturing process, which includes applying a patch of fastening material 40 to web 26, is not included in the process since at least a portion, and up to the entirety, of the major surface of front web portion 26 already includes fastening area properties.

Therefore, a landing zone may or may not have distinct physical edges, depending on whether the fastening properties desired to be performed thereby (i) are provided by distinct separate e.g. web element(s) or (ii) are integral with a surface of front portion web 26.

At segment "CI" of the manufacturing process, first fault line 32 and second fault line 34 are effected on front portion web 26, both fault lines being effected in a fashion substantially perpendicular to machine direction 76. Fault line 32 is disposed laterally of the most remote portion, with relationship to deactivation line 31, of side 42 of fastening area 40. Similarly, fault line 34 is disposed laterally of the most remote portion, with relationship to deactivation line 31, of side 44 of fastening area 40. As with deactivation line 31, fault lines 32, 34 preferably do not extend closer than 0.25 inch from either outer edge 55 or inner edge 56 of front portion web 26, reserving substantial uncut web portions 38, 39 adjacent outer and inner edges 55, 56. Each respective uncut web portion 38, 39 of front portion web 26 is disposed between an end of a respective fault line and a respective adjacent outer or inner edge 55, 56, respectively, of front portion web 26, wherein substantial uncut web portions 38, 39 comprise support connections which, at least in part, aid in maintaining the integrity of front portion web 26.

In some embodiments, first and second fault lines 32, 34 comprise perforations which can extend effectively to outer edge 55 and/or inner edge 56 of front portion web 26, thus reserving no separately defined substantial uncut web portions 38, 39 adjacent outer and inner edges 55, 56.

As used herein, "substantial uncut web portions" means web portions of significantly greater substance than uncut web portions located between perforations in the same fault line.

"Fault line," as used in the discussion of FIG. 1A, includes a wide variety of structures which substantially weaken the machine direction strength of the web at the fault line, and can include, for example, a line of perforations, a cut line bounded on opposing ends by perforations, and/or a cut line bounded on opposing ends by uncut material, wherein the length of such cut is at least as great as the length of uncut or un-perforated material at opposing ends of the cut. Other effectively weakening structures will be known to those skilled in the art.

"Fault line perforations" illustrated and referred to herein can take on a variety of configurations. For example and without limitation, such configurations can include straight line slits, curved line slits; lines of multiple straight, curved, or angled slits wherein the slits are aligned with the direction of extension of the fault line; lines of multiple straight, curved, or angled slits wherein the slits are directed at angles to the direction of extension of the fault line. The fault line perforations can also comprise small cut-outs of the material of the front portion web, wherein the cut-outs can have any of a variety of shapes including circular, oval, square, rectangular, other polygonal shapes, star shapes, and the like. Further, the perforations can comprise a combination of the above configurations and shapes.

Fault lines 32, 34 can be affected using a variety of devices including, but not limited to, rotary die cutter, knife cutter, paired rotary horn and anvil, and other faulting means known to those skilled in the art.

Generally, where elastics in an elasticized web are stretched in the machine direction, and the stretched web is severed across the transverse width of the web thus to create a transversely extending free edge, the web tends to retract when such severance takes place. When such severance occurs before e.g. the fastening area material or tab components can be attached, the resulting retraction increases the complexity of making such attachments. Since no such transverse severances are made across elasticized web 26 in the invention, the integrity of the web is maintained while the fastening area material and fasteners are implemented on the web to, among other functions, assist in maintaining the integrity of the web.

Figure 3A:
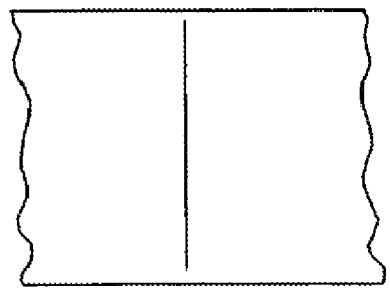
FIGS. 3A-3H illustrates exemplary fault line structures.
Figure 3B:
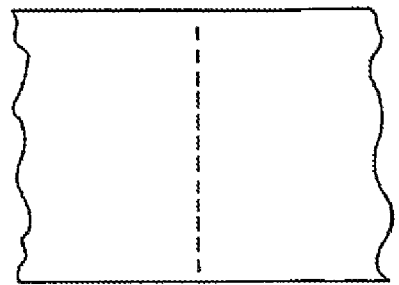
Figure 3C:
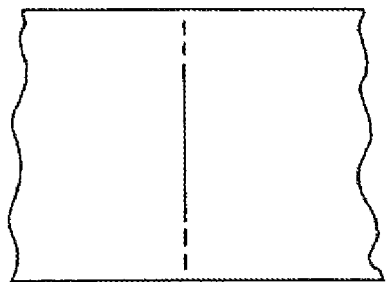
Figure 3D:
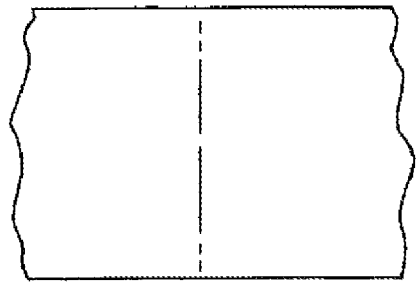
Figure 3E:
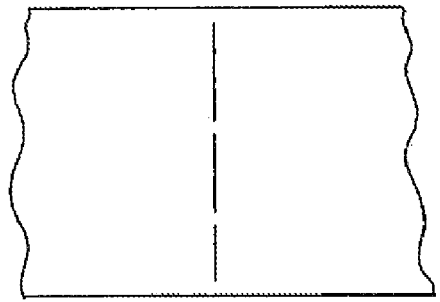
Figure 3F:
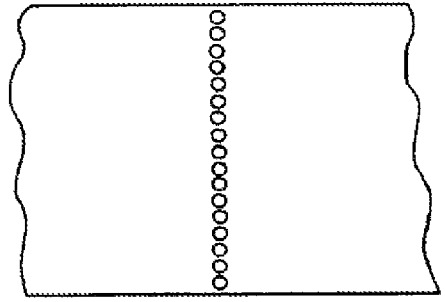
Figure 3G:
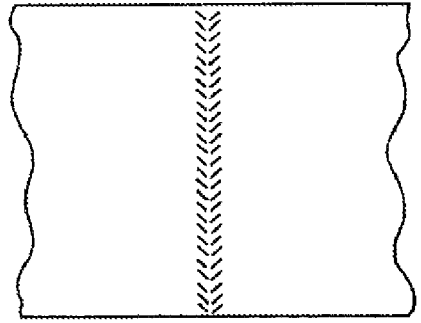
Figure 3H:
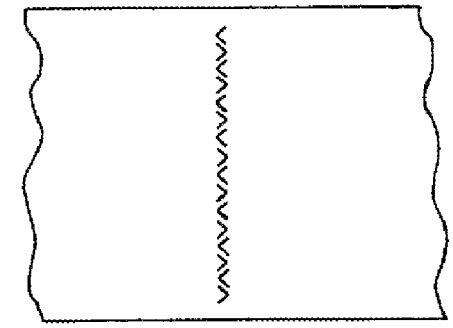

The structure of fault lines 32, 34 can be selected as desired so long as the fault lines are sufficiently strong to tolerate the process segments "CI" and "DI" prior to emplacement of fasteners 66, 68 thereby to reinforce the front portion web across fault lines 32, 34. FIGS. 3A-3H illustrates representative structures for fault lines 32, 34. FIG. 3A represents a single straight line cut through web 26. FIG. 38 represents a line of uniformly configured and uniformly spaced perforations. FIG. 3C represents a single elongate cut and shorter-length perforations at each end of the elongate cut and aligned with the elongate cut. FIG. 3D represents two aligned elongate cuts and shorter perforations at opposing ends of the fault line. FIG. 3E represents three elongate cuts, aligned with each other, with the illustrated bridging material between respective ones of the elongate cuts. FIG. 3F illustrates a fault line wherein the weakness in the fault line is developed by removing small circular bits of web material such that the fault line is represented by an array of cooperating apertures. Such apertures can have a variety of shapes, such as circular, square, rectangular, other polygonal shape, star-shape, and the like. FIG. 3G illustrates a fault line defined by perforations disposed at an angle to the direction of extension of the fault line. FIG. 3H illustrates a fault line defined by angled slits directed at angles to the direction of extension of the fault line.

Any of the line structures illustrated or made obvious herein can be affected by forming cuts through the material of web 26. In the alternative, satisfactory fault line structures can be obtained by crushing the material of web 26 in a respective line pattern suitable to develop a desired level of weakness across the respective fault line.

At segment "DI" of the manufacturing process illustrated in FIG. 1A, first fastener 66 is disposed on front portion web 26 overlying at least a portion of fastening area 40 and extending across first fault line 32. Similarly, second fastener 68 is disposed on front portion web 26 overlying at least a portion of fastening area 40 and extending across second fault line 34. Some embodiments comprise fasteners which effectively span from inner edge 56 to outer edge 55 of front portion web 26, such fasteners preferably being cut and trimmed in a subsequent step of the process.

Referring specifically to second fastener 68 at segment "DI" to define features common to fasteners of the invention, the location of second fastener 68 is such that a floating portion 47 of fastener 68, unattached to either web 26 or fastening area 40, overlies an area of front portion web 26 between second side 44 of fastening area 40 and second fault line 34. The portion of second fastener 68 which overlies a portion of fastening area 40 comprises adjusting portion 49, which, at least in part, cooperatively forms an engagement relationship with fastener receptors in fastening area 40. Base portion 43 of second fastener 68 is disposed at a portion of second fastener 68 most remote from adjusting portion 49. Base portion 43 of second fastener 68 is generally permanently affixed to front portion web 26 remote from fastening area 40 and outside second fault line 34, namely with second fault line 34 between fastening area 40 and base portion 43. Base portions 43 of respective fasteners are affixed to front portion web 26 preferably using adhesive and/or ultrasonic bonding, although other affixation means known to those skilled in the art are contemplated.

Fasteners 66, 68 as illustrated herein define attachment structures which, e.g. in combination with fastening area 40, or the like, can be repeatedly fastened, released, adjusted and re-fastened. Acceptable embodiments of fasteners 66, 68 can include any material capable of forming cooperative engagement relationships with the respective material used for fastening area 40. For example and without limitation, such acceptable fastener materials are adhesives, cohesives, mechanical fasteners such as buttons and corresponding buttonholes, snaps and the like, as well as other fasteners which can be repeatedly fastened and released known to those skilled in the art. Mechanical hook and loop fasteners are preferred because of their associated versatility and cost effectiveness.

Figure 2A:
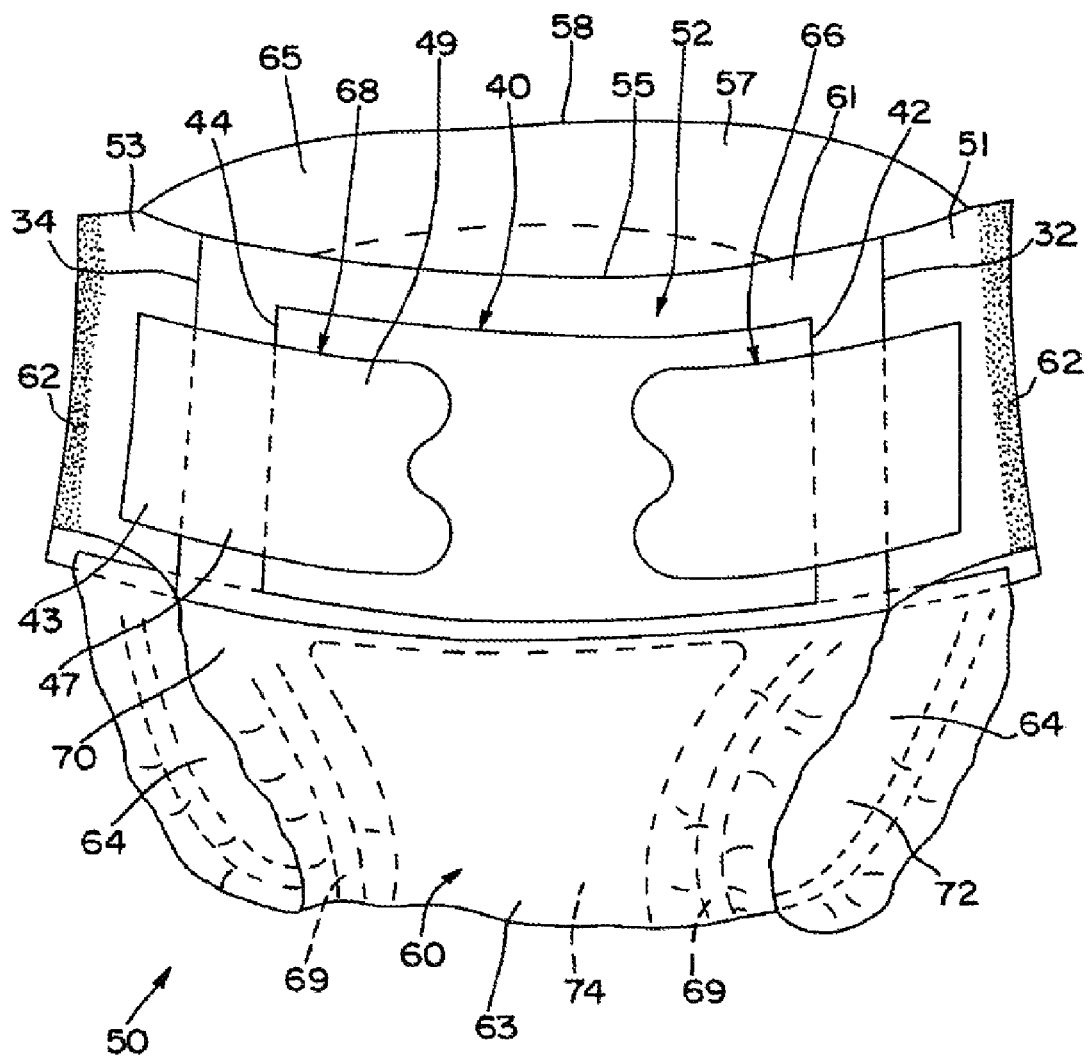
FIG. 2A shows an elevated pictorial view of a representative personal care article of methods of FIG. 1A.

At segment "EI" of the manufacturing process, crotch element 60 is attached to front portion web 26 of web sausage 22 at least at or near inner edge 56 of front portion web 26, and to rear portion web 28 of web sausage 22 at least at or near inner edge 59 of rear portion web 28. In the illustrated embodiment, crotch element 60 is attached to surfaces of webs 26, 28 which surfaces are directed away from the viewer. Accordingly, crotch element 60 is shown in dashed outline at the respective webs 26, 28. FIG. 2A shows crotch element 60 in solid outline.

Crotch element 60 generally comprises absorbent core 74 and leg elastic 69 (FIG. 2A), although such components can be added to crotch element 60 of web sausage 22 during other portions of the manufacturing process. Crotch element 60 is preferably attached to front portion web 26 and rear portion web 28 via adhesives, although other attachment means known to those skilled in the art are contemplated.

As used herein, "web sausage" includes single and multiple webs, or multiple web elements and components thereof, used as basis or other substrate upon which to build personal care article workpieces. Where multiple webs are used, a second such multiple web can overlie a first such web, or, as illustrated in FIG. 1A, first and second webs can be advanced in a side-by-side, spaced from each other, arrangement.

At segment "FI" of the manufacturing process, leg cut-outs 36 are separated from front portion web 26 using e.g. a rotary die cutter as indicated by excision arrow 78. The removal of leg cut-outs 36 also disassociates uncut web portions 39 originally disposed at inner edge 56 of front portion web 26, from front portion web 26, thus disabling support connections across fault lines 32, 34 and completing the severance of respective fault lines 32, 34 on first inner edge 56. Separation of the leg cut-outs also develops a preferred edge configuration for crotch element 60 thus to define a crotch portion 63 of FIG. 2A extending between web 26 and web 28.

At segment "GI" of the manufacturing process, the web sausage is folded at crotch portion 63 such that front portion web 26 and rear portion web 28 are disposed in an overlying relationship with one another wherein respective outer edges 55, 58 of respective webs 26, 28 preferably, but not necessarily, are substantially overlying one another. Such folding of web sausage can be effected using a folding mechanism such as, but not limited to, a helical folder or a folding bar.

At segment "HI" of the manufacturing process, side seam bonds 62 are formed adhering front portion web 26 to rear portion web 28 between adjacent fault lines of respective adjacent individual workpiece precursors 24. Bonds 62 are preferably formed using ultrasonic energy applied by e.g. ultrasonic bonding apparatus. As an alternative to ultrasonic energy, side seam bonds 62 can be implemented using e.g. thermal energy, chemical adhesives, or a combination of chemical adhesives with ultrasonic energy or thermal energy.

At segment "II" of the manufacturing process, waist trim composite 41 is separated from workpiece precursors 24 using e.g. a slitter apparatus, thus removing a strip of material at and adjacent outer edge 55 of front portion web 26 and any of rear portion web 28 which underlies the removed strip of front portion web 26. The removal of waist trim composite 41 also disassociates respective uncut web portions 38, originally disposed near respective outer edge 55 of the front portion web, from the front portion web, thus disabling support connections provided by such uncut web portions and completing the severance of the front portion web at respective fault lines 32, 34. Accordingly, once trim composite 41 is removed, fasteners 66, 68 provide primary support of front portion web 26 against machine direction stresses across fault lines 32, 34. Where fault lines 32, 34 represent continuous cut lines cut entirely through the thickness of web 26, fasteners 66, 68 provide all support of the front portion with respect to machine direction stresses across fault lines 32, 34. Where fault lines 32, 34 include support connections or bridges such as uncut areas between perforations elements of a line of perforations, the machine direction support can be shared between such uncut areas and fasteners 66, 68.

At segment "JI" of the manufacturing process, individual workpiece precursors 24 are preferably severed from the web sausage thus to define individual separate and discrete finished personal care products. Such severing can be effected by a cutting in a cross-machine direction along each respective side seam 62 using e.g. a knife and anvil cut-off. Such cut is made between edges 67A, 67B so as to define a bonded such side seam on each of the products so defined by the respective cuts. Such a cut is representatively illustrated as line 80.

Rather than severing or separating individual personal care articles at side seams 62 as illustrated, the respective side seam cut lines can be affected, instead, as lines of weakness such as are illustrated in FIGS. 3A-3H, with complete severance at every "n" workpieces. Such process results in strips of respective personal care articles, each strip containing "n" personal care articles. The strip can then be rolled up for packaging. The user tears a personal care article off the strip for use as desired.

Figure 1B:
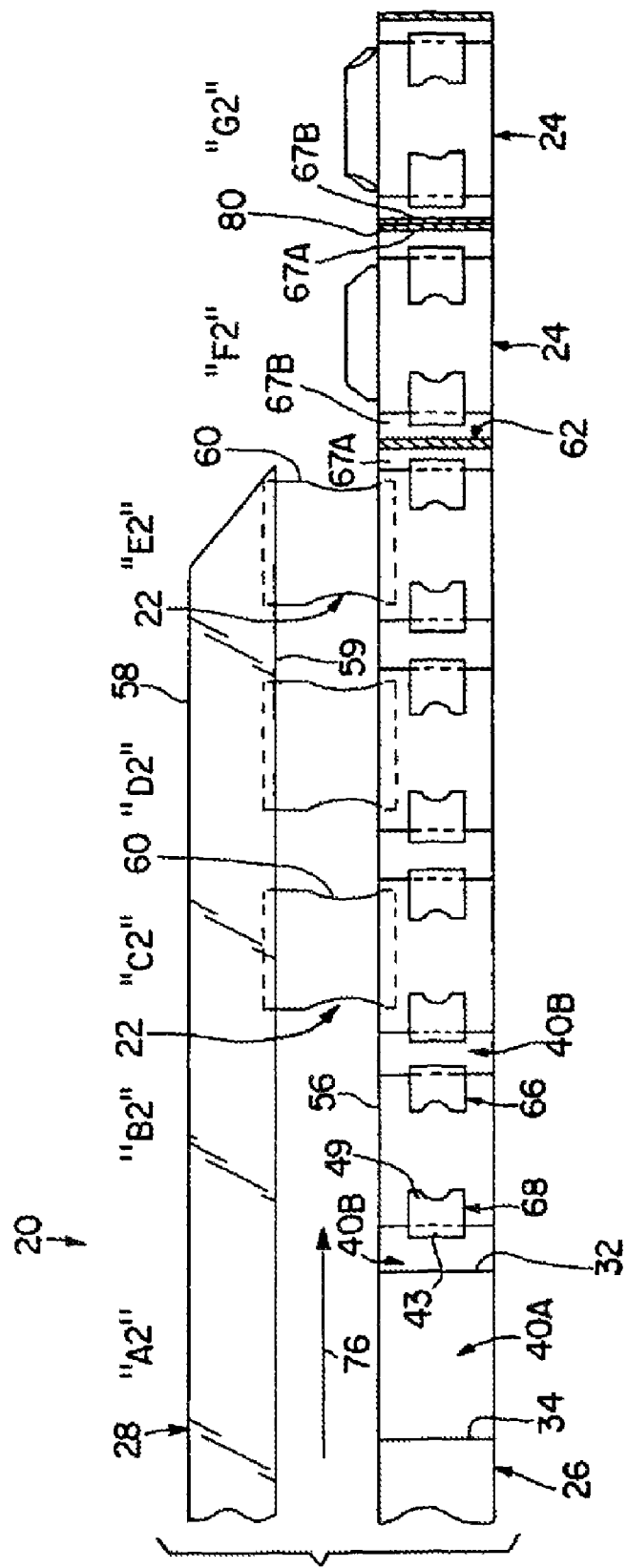
FIG. 1B shows another representative top view of a stream of workpieces indicative of other methods of the invention.
Figure 2B:
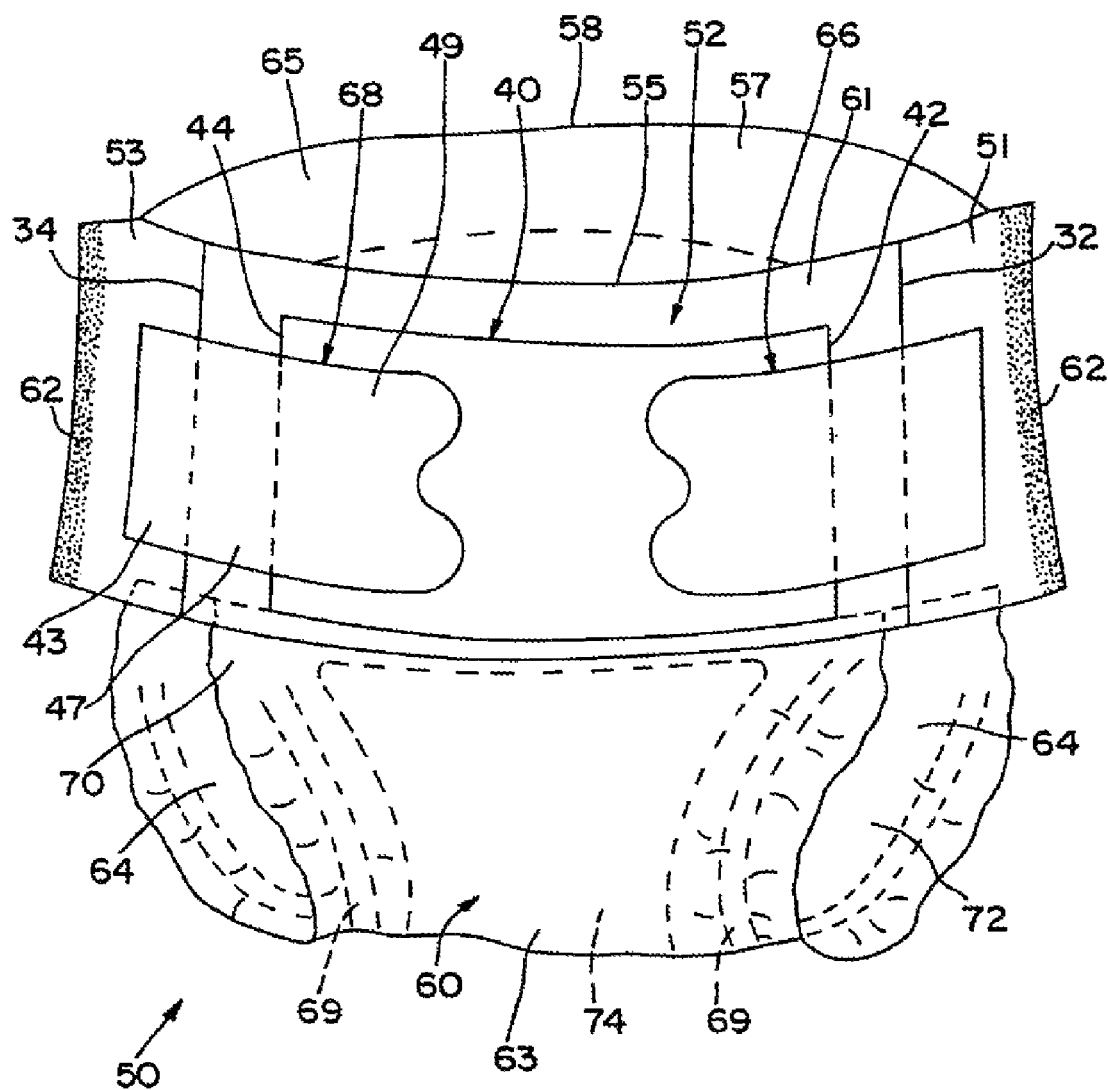
FIG. 2B shows an elevated pictorial view of a representative personal care article of methods of FIG. 1B.

Referring to FIG. 1B, the invention comprehends yet other embodiments of apparatus and methods for assembling personal care absorbent articles. FIG. 2B Illustrates a personal care absorbent article 50 manufactured from the methods of FIG. 1B. Respective segments of the exemplary manufacturing process illustrated in FIG. 1B are indicated by letters "A2-G2".

At the segment of the method illustrated at "A2", a stream of workpieces 20 travels along a manufacturing path in the machine direction indicated by directional arrow 76. In the embodiment illustrated in FIG. 1B, stream of workpieces 20 is defined in the combination of front portion web 26 and rear portion web 28, as well as any other personal care article components employed or affixed, both directly and indirectly, to such webs.

In some embodiments, one or both front portion web 26 and back portion web 28 comprise web material which demonstrates resiliently stretchable properties such as stretch-bonded laminate material and/or neck-bonded laminate material, as well as other composite elastomeric materials and/or resiliently stretchable materials known to those of ordinary skill in the art. Other embodiments can comprise elastic at least in and/or on portions of one or both of front portion web 26 and rear portion web 28. Other less preferable embodiments comprise little or no elastic in and/or on one or both front portion web 26 and rear portion web 28.

Front portion web 26 is preferably constructed from a material which demonstrates landing zone properties capable of forming engagement relationships with respective fastener materials defined in step "D" of the process of FIG. 1A. In such preferred embodiments, at least a portion, and up to the entirety, of the major surface of front web portion 26 already include fastening area properties. In other less preferable embodiments of the process illustrated in FIG. 1B, a patch of landing zone material may be placed on front portion web 26 as demonstrated and described in segment "BI" of FIG. 1A.

Therefore, as with apparatus and methods of FIG. 1A, apparatus and methods of FIG. 1B also have a landing zone which may or may not have distinct physical edges, depending on whether the fastening properties desired to be performed thereby (i) are provided by distinct separate e.g. web element(s) or (ii) are integral with a surface of front portion web 26. Thus in any of the embodiments of the invention, a fastening area can be defined in front portion web 26 by applying a separate landing zone patch, by applying a layer of material or coating over front portion web 26 to give it landing zone properties, or by utilizing a material as front portion web 26 which inherently possesses landing zone characteristics. Still referring to segment "A2" of FIG. 1B, first fault line 32 and second fault line 34 are affected on front portion web 26, both fault lines being affected in a fashion substantially perpendicular to machine direction 76. Fault lines 32, 34 preferably extend completely to outer edge 55 and inner edge 56 of front portion web 26, thereby reserving no substantial uncut web portions adjacent outer and inner edges 55, 56.

"Fault line," as used in the discussion of FIG. 1B, includes a wide variety of structures which weaken the machine direction strength of the web at the fault line but provide sufficient support to maintain the integrity of the web as such web is manipulated during the manufacturing process. A fault line of the methods of FIG. 1B, unlike the methods of FIG. 1A, does not have substantial uncut web portions located near/at the inner and/or outer edge of the front portion web. A fault line of FIG. 1B can include, for example, a line of perforations, a line of segmented/interrupted cuts, a line of a combination of perforations and segmented/interrupted cuts, and/or any other known means of creating a fault line that results in a weakening of the machine direction strength of the web, yet provides sufficient support to maintain the integrity of the web as such web is manipulated during the manufacturing process.

As with the methods of FIG. 1A, the "fault line perforations" of FIG. 1B can take on a variety of configurations. For example and without limitation, such configurations can include straight line slits, curved line slits; lines of multiple straight, curved, or angled slits wherein the slits are aligned with the direction of extension of the fault line: lines of multiple straight, curved, or angled slits wherein the slits are directed at angles to the direction of extension of the fault line. The fault line perforations of FIG. 1B can also comprise small cut-outs of the material of the front portion web, wherein the cut-outs can have any of a variety of shapes including circular, oval, square, rectangular, other polygonal shapes, star shapes, and the like.

Further, the perforations can comprise a combination of the above configurations and shapes. Any of the line structures illustrated or made obvious therein can be affected by forming cuts through the material of web 26. In the alternative, satisfactory fault line structures can be obtained by crushing the material of web 26 in a respective line pattern suitable to develop a desired level of weakness across the respective fault line.

The structure of fault lines 32, 34 can be selected as desired so long as the fault lines are sufficiently strong to tolerate at least process segment "B2" prior to emplacement of fasteners 66, 68 thereby to reinforce front portion web 26 across fault lines 32, 34. In other words, points of web-attachment, in combination, are sufficient to maintain the integrity and/or uniformity of the web 26 as such web proceeds through the process of manufacture, wherein each point of web-attachment is defined between adjacent cuts and/or perforations on a respective fault line.

At segment "B2" of the manufacturing process illustrated in FIG. 1B, first fastener 66 is disposed on front portion web 26 extending across first fault line 32. Similarly, second fastener 68 is disposed on front portion web 26 extending across second fault line 34. Some embodiments comprise fasteners which effectively span from inner edge 56 to outer edge 55 of front portion web 26.

Referring specifically to second fastener 68 at segment "B2" to define features common to fasteners of the invention, the location of second fastener 68 is such that a portion of second fastener 68 which overlies a portion of central fastening area 40A comprises adjusting portion 49, which, at least in part, cooperatively forms an engagement relationship with fastener receptors inherent to front portion web 26 in fastening area 40A. Base portion 43 of second fastener 68 is disposed at a portion of second fastener 68 most remote from adjusting portion 49. Base portion 43 of second fastener 68 is generally permanently affixed to peripheral fastening area 40B of front portion web 26 remote from central fastening area 40A and outside second fault line 34, namely with second fault line 34 between central fastening area 40A and base portion 43. Base portions 43 of respective fasteners are affixed to peripheral fastening areas 40B of front portion web 26 preferably using adhesive and/or ultrasonic bonding, although other affixation means known to those skilled in the art are contemplated.

Fasteners 66, 68 as illustrated herein define attachment structures which, e.g. in combination with central fastening area 40A and/or peripheral fastening area 40B, or the like, can be repeatedly fastened, released, adjusted and re-fastened. Acceptable embodiments of fasteners 66, 68 can include any material capable of forming cooperative engagement relationships with the respective material used for fastening areas 40A, 40B. For example and without limitation, such acceptable fastener materials are adhesives, cohesives, mechanical fasteners such as buttons and corresponding buttonholes, snaps and the like, as well as other fasteners which can be repeatedly fastened and released known to those skilled in the art. Mechanical hook and loop fasteners are preferred because of their associated versatility and cost effectiveness.

At segment "C2" of the manufacturing process illustrated in FIG. 1B, crotch element 60 is attached to front portion web 26 of web sausage 22 at least at or near inner edge 56 of front portion web 26, and to rear portion web 28 of web sausage 22 at least at or near inner edge 59 of rear portion web 28. In the illustrated embodiment, crotch element 60 is attached to surfaces of webs 26, 28 which surfaces are directed away from the viewer. Accordingly, crotch element 60 is shown in dashed outline at the respective webs 26, 28. FIG. 2B shows crotch element 60 in solid outline.

At segment "D2" of the manufacturing process, a leg cut-out, e.g. 36 as in segment FI of the methods of FIG. 1A, can be affected as an optional step. Referring to FIG. 1B, since lines of weakness 32, 34 effectively span the entirety of the cross-machine direction width of front portion web 26, no substantial uncut web portion (39 of FIG. 1A) need be removed. Thus, step "D2" of the manufacturing process illustrated in FIG. 1B is included merely to signify that other fabrication steps known to those of ordinary skill in the art, e.g. effecting leg cut-outs, are not essential, but are contemplated in methods of the invention, e.g. for comfort of the wearer and, correspondingly, consumer preference.

At segment "E2" of the manufacturing process illustrated in FIG. 1B, the web sausage is folded at crotch portion 60 such that front portion web 26 and rear portion web 28 are disposed in an overlying relationship with one another wherein respective outer edges 55, 58 of respective webs 26, 28 are preferably, but not necessarily, substantially overlying one another. Such folding of web sausage can be effected using a folding mechanism such as, but not limited to, a helical folder or a folding bar.

At segment "F2" of the manufacturing process, side seam bonds 62 are formed adhering front portion web 26 to rear portion web 28 between adjacent fault lines of respective adjacent individual workpiece precursors 24. Bonds 62 are preferably formed using ultrasonic energy applied by e.g. ultrasonic bonding apparatus. As an alternative to ultrasonic energy, side seam bonds 62 can be implemented using e.g. thermal energy, chemical adhesives, or a combination of chemical adhesives with ultrasonic energy or thermal energy.

At segment "G2" of the manufacturing process, individual workpiece precursors 24 are preferably severed from the web sausage thus to define individual separate and discrete finished personal care products. Such severing can be effected by a cutting in a cross-machine direction along each respective side seam 62 using e.g. a knife and anvil cut-off. Such cut is made between edges 67A, 67B so as to define a bonded such side seam on each of the products so defined by the respective cuts. Such a cut is representatively illustrated as line 80.

Rather than severing or separating individual personal care articles at side seams 62 as illustrated, the respective side seam cut lines can be affected, instead, as lines of weakness such as are illustrated in FIGS. 3A-3H, with complete severance at every "n" workpieces. Such process results in strips of respective personal care articles, each strip containing "n" personal care articles. The strip can then be rolled up for packaging. The user tears a personal care article off the strip for use as desired.

In other preferred embodiments of FIG. 1B, web 26 travels along direction of manufacture 76 on a conveyor, roll, or the like, which maintains the relative positioning of web 26 with respect to such conveyor or roll by e.g. vacuum, suction, static forces, or any other means known in the art for maintaining the relative positioning of a web on a roll or conveyor at least until fasteners 66, 68 are applied to web 26. In such other preferred embodiments of FIG. 1B, fault lines 32, 34 can comprise any of the above discussed embodiments of fault lines as well as a complete severance across the entirety of web 26. The roll or conveyor used in such embodiments sustains the positioning of a respective central fastening area 40A relative to adjacent upstream and downstream peripheral fastening areas 40B, such that fasteners 66, 68 can be applied to such areas of web 26 without unwanted overlap, shifting, or spacing of such areas, relative to each other.

In yet other embodiments, the invention comprehends methods of manufacturing personal care absorbent articles in a format which includes defining a stream of workpieces connected to each other along a web sausage having an indefinite length wherein, instead of webs 26, 28 being two separate webs, personal care articles of the invention are fabricated from at least one single, unitary outer layer web which spans in the cross-machine direction from outer rear edge 58 to outer front edge 55 of FIG. 1B. In such embodiments, absorbent cores and bodyside liner web, to cover the absorbent cores, can be applied to the stream of workpieces before, during, or after method segments described in FIGS. 1A and 1B. In such unitary-web embodiments, leg cut-outs are mandatory between adjacent workpieces to create a more consumer-accepted e.g. hour-glass configuration of the crotch portion of each resulting personal care article. In such unitary-web embodiments, the implementation of fault lines 32, 34, the application of fasteners 66, 68, the folding of the stream of workpieces, and the side seam bonding of each respective workpiece are all necessary steps.

Thus, manufacturing processes of the invention achieve novel methods of manufacturing personal care articles by maintaining a stream of workpieces, connected to each other in a web sausage, without severing respective front portions and rear portions from respective front and rear precursor webs until relatively late in the process, with respect to conventional methods, thereby enabling manufacturers of personal care articles to integrate personal care article components into the web sausage in the context of a continuous web of workpieces rather than individual workpiece precursors, while manufacturing a refastenable personal care product having separated or effectively weakened fault lines between fastening area 40 and side seams 62. Such methods of the invention result in minimizing waste as well as improving manufacturing efficiency.

Along with methods of manufacture, the present invention also relates to the resultant personal care articles made by such methods of manufacture. While the preferred embodiments of the present invention are described herein in terms of a personal care article such as a pull-on pant or an adult incontinence brief, the invention includes, and is equally applicable to, infant diapers, training pants, and the like.

FIGS. 2A and 2B illustrate personal care articles 50 manufactured using the methods of FIGS. 1A and 1B, respectively, Such personal care articles include a front portion 52 having a central section 61, a first lateral section 51, a second lateral section 53, and a front edge 55, a rear portion 57 having a rear edge 58, and a crotch portion 63. Additionally, personal care article 50 also comprises an absorbent core 74 mounted between a bodyside liner 72 and an outer cover 70. Fastening area 40 is disposed at an outer surface e.g. of central section 61 of front portion 52 and cooperates with first fastener 66 and second fastener 68 in creating a cooperative engagement relationship. Such engagement relationship enables a user to fasten, unfasten and re-fasten fasteners 66, 68 on fastening area 40 thereby to adjust waist sizing of the personal care article. During use, and preferably as packaged, each of the fasteners, e.g. second fastener 68, is releasably secured to fastening area 40 at adjusting portion 49 of the fastener, is non-releasably secured to second lateral section 53 of front portion 52 outwardly of fault line 34 at base portion 43 of the fastener, and is unsecured to front portion 52 between fastening area 40 and fault line 34 at floating portion 47 of the fastener.

Leg elastics 69 are shown extending generally from the areas peripheral to opposing sides of absorbent core 74, following the contour of the personal care article 50, through crotch portion 63 and ending at or near front portion 52 and rear portion 57. Leg elastics 69 function to gather the material at the side edges of crotch portion 63 along leg openings 64. Leg openings 64 are formed as apertures in the personal care article as front portion 52 is secured to rear portion 57 to form side seams 62 thus to form, as in FIGS. 1A and 1B, personal care articles e.g. as illustrated in FIGS. 2A and 2B, respectively.

Various types of elastic materials are known for use in leg elastics 69. Leg elastics 69 typically provide overall retractive tensions of from about 10 grams to about 400 grams on a given leg opening at stretch-to-stop conditions. Preferably, leg elastics 69 provide tensions of about 50 grams to about 220 grams. More preferably, leg elastics 69 provide tensions of about 80 grams to about 200 grams.

A variety of materials can be employed as webs 26, 28 and/or web sausage 22 components illustrated in FIGS. 1A and 1B, in comprising personal care articles of the invention. Various woven and nonwoven fabrics can be used for bodyside liner 72. For example, bodyside liner 72 can be e.g. a meltblown or spunbonded or other non-woven web of polymeric material selected from the group consisting of polyolefins including polyethylenes and polypropylenes, polyesters, and polyamides, and mixtures, copolymers, and blends of such polymeric fibers. Bodyside liner 72 can also comprise a carded and/or bonded web composed of natural and/or synthetic fibers. The bodyside liner can be composed of a substantially hydrophobic material wherein the hydrophobic material is treated with a surfactant or otherwise processed to impart a desired level of wettability and hydrophilicity.

Bodyside liner 72 can comprise nonwoven, spunbonded, polypropylene fabric fabricated with 2.8-3.2 denier fibers, formed into a web having a basis weight of e.g. about 22 grams per square meter and a density of e.g. about 0.06 grams per cubic centimeter. The fabric is preferably surface treated with e.g. about 0.3 weight percent of a surfactant. Bodyside liner 72 typically comprises a fibrous web defining a multiplicity of small e.g. microporous openings randomly spaced between the fibers and according to location and orientation of the fibers, extending from a major surface of the web into the interior of the web. Such small openings typically extend through the entirety of the thickness of the web.

Addressing structure, bodyside liner 72 can be fabricated using material selected from the group consisting of porous foams, reticulated foams, apertured polymeric films, polymeric fibers, and natural fibers. Bodyside liner 72 can comprise a multiplicity of components or layers which correspond to any of the materials disclosed herein, as well as others known in the art.

It is generally preferred that outer cover 70 of the personal care article be formed from a material which is substantially impermeable to liquids. A typical outer cover 70 can be manufactured from a thin plastic film or other flexible liquid-impermeable material. For example, outer cover 70 can be formed from a film of polymeric material selected from the group consisting of polyolefins including polyethylenes and polypropylenes, polyesters, and polyamides, and mixtures, copolymers, and blends of such polymeric materials, having thicknesses, for example, of from about 0.012 millimeter to about 0.13 millimeter.

In embodiments where outer cover 70 should have a more cloth-like feel, the outer cover can comprise a polyethylene film having a nonwoven web, such as a spunbonded web of polyolefin fibers, bonded to a surface thereof. For example, a polyethylene film having a thickness of about 0.015 millimeter can have thermally or otherwise bonded thereto a spunbonded web of polyolefin fibers having fiber thicknesses of from about 1.5 to about 2.5 denier per filament, which spunbonded web has a basis weight of e.g. about 24 grams per square meter.

Further, outer cover 70 can be formed of a woven or nonwoven fibrous web which has been totally or partially constructed or treated to impart a desired level of liquid impermeability to selected regions which are e.g. adjacent or proximate absorbent core 74.

Still further, outer cover 70 can optionally be composed of a microporous material which permits vapors to escape from absorbent core 74 and through outer cover 70 while preventing liquid exudates from passing through the outer cover.

One or both of outer cover 70 and bodyside liner 72 can comprise a fibrous web defining a multiplicity of randomly-spaced small openings extending from a major surface of the web into the interior of the web. Polymeric material such as the recited polyolefins including polyethylenes and polypropylenes, polyesters, and polyamides, and mixtures, copolymers, and blends of such polymeric materials can be used in either film form or in non-woven fiber form, for one or both of bodyside liner 72 and outer cover 70. As to bodyside liner 72, films are apertured films. As to outer cover 70, fibrous webs are impermeable to e.g. aqueous liquid.

Included in the definition of polymeric material above are all routine, common, normal additives known to those skilled in the art of polymeric materials such as processing aids, chemical stabilizers, compatibilizers e.g. where more than one polymer is used, fillers, and the like.

Absorbent core 74 suitably comprises hydrophilic fibers, such as a web or matt or loose collection of cellulosic fluff, in combination with a high-absorbency material commonly known as superabsorbent material. Absorbent core 74 preferably comprises a mixture of superabsorbent hydrogel-forming particles and wood pulp fluff. In place of the wood pulp fluff, one can use synthetic, polymeric, meltblown fibers or a combination of meltblown fibers and natural fibers. The superabsorbent material can be substantially homogeneously mixed with the hydrophilic fibers or can be otherwise combined into absorbent core 74.

Alternatively, absorbent core 74 can comprise a laminate of fibrous webs and superabsorbent material or other suitable means of maintaining a superabsorbent material in a localized area. Absorbent core 74 can additionally comprise an uncreped through air dried paper web material known as UCTAD.

Absorbent core 74 can have any of a number of shapes. For example and without limitation, absorbent core 74 can be rectangular, I-shaped or T-shaped. In such products as e.g. refastenable absorbent articles, pants, and the like, absorbent core 74 is preferably narrower in the crotch portion than in the rear portion or the front portion, especially where the crotch portion of the personal care article is narrower than the rear portion or the front portion.

The high-absorbency material in absorbent core 74 can be selected from natural, synthetic and modified natural polymers and materials. The high absorbency material can be inorganic material, such as silica gels, or organic compounds, such as cross-linked polymers. The high absorbency material refers to any structure or composition, along with associated process, which renders normally water-soluble material substantially water insoluble but swellable, whereby absorbent properties are available but the swelled material is substantially immobile after absorbing water-based liquid.

Such superabsorbent material can be fabricated by creating e.g. physical entanglement, crystalline domains, covalent bonds, ionic complexes and associations, hydrophilic associations such as hydrogen bonding, and hydrophobic associations, or Van der Waals forces. Two such superabsorbents are DRYTECH® 2035 M and FAVOR® SXM 880. DRYTECH® available from the Dow Chemical Company, Midland, Mich. FAVOR® is available from Stockhausen, Inc., Greensboro, N.C.

Personal care articles of the invention can be used in at least two different ways. First, personal care article 50 of FIGS. 2A and/or 2B, as shipped to the customer, can be used as a pant-type structure. In such format, first and second fasteners 66, 68, respectively, are, and remain, attached separately to fastening area 40 of front portion 52. The pant-type structure is slipped onto the wearer while retaining attachment of first and second fasteners 66, 68 to fastening area 40 of personal care article 50 through a cooperative engagement relationship.

Accordingly, the legs of the wearer are inserted through waist opening 65, and through leg openings 64. The pant is then pulled in a cephalic direction until leg openings 64 are snugly positioned at the groin of the wearer. The user can adjust the fitting of the pant-type structure to create a better relative positioning of the waist portion of the respective personal care article about the torso of the wearer, directed toward comfort of the wearer, thus to improve the fit.

Further adjusting to obtain a tighter or looser fit can be accomplished by the user by subsequent grasping and pulling of first and/or second fasteners 66, 68, away from fastening area 40, thereby to disengage first and/or second fasteners 66, 68 from fastening area 40. Respective fasteners 66, 68, are then moved over desired locations on fastening area 40 and re-engaged to fastening area 40, so as to achieve the desired relationship between adjusted size of personal care article 50 and size of the wearer. Release and re-fastening of fasteners 66, 68 can occur multiple times, e.g. an indeterminate number of times, to enable proper fitting throughout the expected use life of the personal care article. Fasteners 66, 68 can be adjusted individually or in combination with each other to create a relatively tighter or relatively looser fit.

Preferably, and as a user convenience, personal care articles of the invention are packaged having respective adjustment portions 49 of first and second fasteners 66, 68, cooperatively affixed in an engagement relationship with fastening area 40, whereby personal care articles of the invention can be mounted on a wearer in a similar fashion to that of conventional pull-on pants.

The second method of using personal care article 50 of FIGS. 2A and/or 2B is to use such article as a diaper-like article. In use as a diaper-like article and before any mounting on the prospective wearer, first and second fasteners 66, 68 are separated from fastening area 40 of personal care article 50, and front portion 52 is pulled away from rear portion 57. In the method of using such article as a diaper-like article, the separation of first and second fasteners 66, 68 from fastening area 40 can be performed before packaging by the manufacturer, or can be performed anytime prior to or during use by the user.

Where fault lines 32, 34 in the personal care article comprise bridging elements of web material bridging across a fault line as in FIGS. 3B-3H, such bridging elements are broken substantially concurrently with separation of fasteners 66, 68 from fastening area 40, thus to completely release lateral sections 51, 53 from central section 61 of the front portion.

After fasteners 66, 68 are separated from fastening area 40, and fault lines 32, 34 are released as necessary, the personal care article is laid on a preferably horizontal surface with bodyside liner 72 facing upwardly. The dorsocaudal portion of the torso of the wearer, e.g. infant or adult, is then laid or otherwise moved onto rear portion 57 of the personal care article. Front portion 52 is then brought frontwardly between the legs of the wearer and onto the torso of the wearer. First and second fasteners 66, 68 are fastened to fastening area 40, completing mounting of the personal care article onto the wearer. Those skilled in the art will recognize the instant above description as a known method of mounting a diaper-like article on a wearer.

Regardless of use as a pull-on pant or diaper-like article, methods of using personal care articles of the invention preferably reflect first and second lateral sections 51, 53 being distinctly defined separate from central section 61 on respective sides of the absorbent article by first and second fault lines 32, 34, respectively, in order for the user to remove a such article without completely removing such user's slacks or outer pants.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

That which is claimed is:

1. A method of manufacturing personal care absorbent articles from a stream of workpiece precursors connected to each other along a web sausage having an indefinite length, a respective one of the personal care articles having a front portion including a front edge, a rear portion, and a crotch portion, the crotch portion disposed between the front portion and the rear portion, the method comprising:
   (a) defining one of the workpiece precursors in the web sausage, the respective workpiece precursor having a respective one of the front portions, a respective one of the rear portions, and a respective one of the crotch portions;
   (b) defining a fastening area in the front portion for connecting a fastener material thereon;
   (c) forming first and second fault lines in the workpiece precursor on the fastening area, the first and second fault lines extending in a direction between the front portion and the rear portion when a blank of the workpiece precursor is laid out flat;
   (d) applying the fastener material over the first and second fault lines, the applied fastener material extending across the first and second fault lines and being releasably secured to the fastening area, and non-releasably secured to the front portion outwardly of the first and second fault lines on the same workpiece precursor; and
   (e) separating the workpiece precursor with the applied fastener material thereon from the web sausage to create a personal care article, wherein individual workpiece precursors are severed from the web sausage to define individual separate and discrete finished personal care products having the first and second fault lines.

2. A method as in claim 1, including cutting leg cut-outs in the web sausage between the respective workpiece precursor and adjacent workpiece precursors, and correspondingly cutting into the respective fault lines in so cutting the leg cut-outs.

3. A method as in claim 2, wherein each of the first and second fault lines is formed as a cut line of one or more elongate cuts and minor, if any, web connections therebetween, with uncut web portions at opposing ends of the cut line, sufficiently strong, in combination, to support integrity of the front portion across the fault lines, the cutting into the fault lines in cutting the leg cut-outs being effective to remove the uncut web portions adjacent the leg cut-outs and to thereby communicate with the cut line, the method further including separating material along a front edge of the workpiece precursor thereby to form the front edge of the personal care article and to separate the substantial uncut web portion at the front edge and thereby further communicate with the cut line, such that the fastener material provides primary support of the front portion across the fault lines.

4. A method as in claim 2, including forming each of the first and second fault lines as a cut line of one or more elongate cuts and minor, if any, web connections therebetween, with substantial uncut web portions at opposing ends of the fault line, and wherein the cutting into the fault line portion at cutting of the leg cut-out comprehends removing the entirety of the uncut web portion at the respective end of the fault line.

5. A method as in claim 1, including forming each of the first and second fault lines as a cut line of one or more elongate cuts and minor, if any, web connections therebetween, with relatively shorter-length perforation cuts and corresponding effective uncut web support connections between such perforation cuts at opposing ends of the one or more elongate cuts.

6. A method as in claim 5, the method further including separating material along a front edge of the workpiece precursor thereby forming the front edge of the personal care article and thus removing the effective support connections at the front edge, such that the fastener material provides primary support of the front portion across the fault lines.

7. A method as in claim 1, including forming each of the first and second fault lines as a line of uniformly formed and uniformly spaced perforations.

8. A method as in claim 7, including cutting leg cut-outs between the respective workpiece precursor and adjacent workpiece precursors in the web sausage, and correspondingly removing first perforated end portions of the respective fault lines in so cutting the leg cut-outs, and separating material along a front edge of the workpiece precursor and thereby forming the front edge of the personal care article and correspondingly separating second perforated end portions of the respective fault lines at the front edge, such that the fastener material provides substantial support of the front portion across the fault lines in combination with support provided by web connections between respective ones of the perforations.

9. A method as in claim 1, including forming each of the first and second fault lines in the workpiece precursor as a line of uniform perforations or cuts.

10. A method as in claim 1, including forming each of the first and second fault lines in the workpiece precursor as a complete severance across the entirety of the front portion of the workpiece precursor.

11. A method as in claim 1, including employing, as the fastening material, first and second fasteners extending across, and thus bridging, the respective first and second fault lines.

12. A method as in claim 11, including employing, as the fastening material, first and second fasteners extending across, and thus bridging, the respective first and second fault lines, the first and second fasteners employing first fastening material effective to interact with second different fastening material in the fastening area.

* * * * *